United States Patent [19]

Sarantakis

[11] 4,320,051
[45] Mar. 16, 1982

[54] ANALGESIC TRIPEPTIDE AMIDES

[75] Inventor: Dimitrios Sarantakis, West Chester, Pa.

[73] Assignee: American Home Products Corporation, New York, N.Y.

[21] Appl. No.: 179,402

[22] Filed: Aug. 19, 1980

Related U.S. Application Data

[63] Continuation-in-part of Ser. No. 107,292, Dec. 26, 1979, abandoned.

[51] Int. Cl.³ .......................................... C07C 103/52
[52] U.S. Cl. .................................................. 260/112.5 E
[58] Field of Search .................. 260/112.5 E, 112.5 R

[56] References Cited

U.S. PATENT DOCUMENTS 4,251,438  2/1981  Moon .......................... 260/112.5 E

OTHER PUBLICATIONS

J. Hughes et al., Nature 258, 1975, pp. 577–579.
A. Waterfield et al., Nature 260, 1976, pp. 626–627.
Pert et al., Science 194, pp. 330–332 1976.
FEBS Letters 76, No. 1, 1977, 91 and 92.
Nature 268, (1977), 547–549.
Structure–Activity Relationships of Enkephalin Analogs, pp. 111–113.
Structure–Activity Relationships of Enkephalin Analogs and Endorphin Analogs, pp. 96–99.
Life Sciences 21, 559–562, 1977.
Acta. Pharm. Sciences 14, (1977), 14–16.
Life Science 23, 99–104 (1978).
British Journal of Pharmacology 59, 1977.
Life Sciences 18, 1473–1482 (1976).

*Primary Examiner*—Delbert R. Phillips
*Attorney, Agent, or Firm*—Richard K. Jackson

[57] ABSTRACT

The analgesic tripeptide amides of the formula:

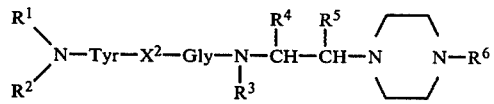

in which
$X^2$ is D-Ala, D-Ser, D-Thr, D-Met, D-Cys, D-Trp, or D-Asn;
$R^1$ is hydrogen, alkyl of 1 to 6 carbon atoms, allyl, cyclopropylmethyl or cyclobutylmethyl;
$R^2$ is hydrogen or alkyl of 1 to 6 carbon atoms;
$R^3$ is hydrogen or alkyl of 1 to 6 carbon atoms;
$R^4$ is isobutyl, cyclohexyl, benzyl, p-halobenzyl or p-nitrobenzyl;
$R^5$ is hydrogen or alkyl of 1 to 6 carbon atoms; and
$R^6$ is hydrogen, alkyl of 1 to 6 carbon atoms, 2-hydroxyethyl, benzyl, diphenylmethyl, phenyl, p-halophenyl, p-nitrophenyl,

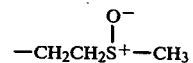

or $-CH_2CH_2SCH_3$;
or a pharmaceutically acceptable salt thereof.

3 Claims, No Drawings

ANALGESIC TRIPEPTIDE AMIDES

RELATED APPLICATIONS

This application is a continuation-in-part of U.S. patent application Ser. No. 107,292 filed Dec. 26, 1979, now abandoned.

BACKGROUND OF THE INVENTION

Enkephalin, a natural opiate receptor agonist in the brain, has been identified [see Hughes et al., *Nature*, 258,577 (1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the stereospecific receptor binding of the opiate antagonist 3H-naloxone in brain homogenates. It has been reported that methionine-enkephalin and leucine-enkephalin, when administered by injection in the brain ventricle in rats, induce a profound analgesia that is fully reversible by naloxone. [See Beluzzi et al., *Nature*, 260, 625 (1976)]. The enkephalins are inactive peripherally, however, and it is believed that the enkephalins are rapidly destroyed by blood enzymes and/or are poorly transported across the blood-brain barrier.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Chang et al., *Life Sciences*, 18, 1473 (1976). Similarly, a long acting synthetic pentapeptide, Tyr-D-Ala-Gly-Phe-Met amide is described in Pert et al., *Science*, 194, 330 (1976); like the natural enkephalins, it is inactive peripherally, for example upon intravenous administration. Baxter et al., British Pharmacological Society Proceedings, Jan. 5-7, 1977, page 455P and 523P, report the i.c.v. activity of Tyr-D-Ala-Gly-Phe-D-Leu. Bajusz et al., FEBS Letters, 76, 91 (1977), by replacing Gly² with D-Met and Met⁵ by Pro-NH₂, obtained a very potent antinociceptive pentapeptide Tyr-D-Met-Gly-Phe-Pro-NH₂ which was 5.5 times more potent than morphine by intravenous administration. Romer et al., Nature, 268, 547 (1977) have shown that:

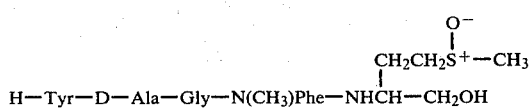

is a potent analgesic when administered peripherally and provides some analgesia when administered orally at high doses (200-300 ng/kg.). Morgan et al., Peptides, Proc. Fifth Amer. Pept. Symp., Ed. Goodman and Meienhofer, p. 111 (1977) reported in vitro and in vivo biological activities of several enkephalin analogs such as N(CH₃)Tyr-Gly-Gly-Phe-Met-NH-propyl. Ling et al., ibid, p. 96 (1977) reported in vitro biological activities of several enkephalin analogs containing D-amino acids in 5-position. Dutta et al., *Life Sciences*, 21, 559 (1977) and Acta. Pharm. Sciences, 14, 14 (1977) described enkephalin analogues containing in 2-position D-Ser, D-Met, D-Ala, D-Thr, D-Lys(Boc), D-Phe, D-Leu, D-Asp and D-Ser (t-Bu) in conjunction with various L-amino acids and other amine in 5-position. belluzzi et al., *Life Sciences*, 23, 99 (1978) have described enkephalin analogues containing D-Ala² and D-Leu⁵ or D-Met.

DESCRIPTION OF THE INVENTION

In accordance with this invention there is provided a group of analgesic tripeptide amides of the formula (I):

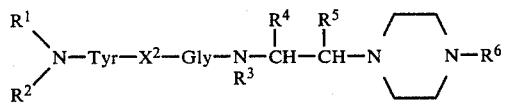

in which
$X^2$ is D-Ala, D-Ser, D-Thr, D-Met, D-Cys, D-Trp or D-Asn;
$R^1$ is hydrogen, alkyl of 1 to 6 carbon atoms, allyl, cyclopropylmethyl or cyclobutylmethyl;
$R^2$ is hydrogen or alkyl of 1 to 6 carbon atoms;
$R^3$ is hydrogen or alkyl of 1 to 6 carbon atoms;
$R^4$ is isobutyl, cyclohexyl, benzyl, p-halobenzyl or p-nitrobenzyl;
$R^5$ is hydrogen or alkyl of 1 to 6 carbon atoms; and
$R^6$ is hydrogen, alkyl of 1 to 6 carbon atoms, 2-hydroxyethyl, benzyl diphenylmethyl, phenyl, p-halophenyl, p-nitrophenyl, —CH₂CH₂SCH₃,

or a pharmaceutically acceptable salt thereof.

In the description of the compound genus of this invention, where $R^4$ and $R^6$ is halophenyl, halo may be Cl, Br, I, or F. The pharmaceutically acceptable salts contemplated are derived from either organic or inorganic acids such as hydrochloric, phosphoric, maleic, acetic, citric, succinic, malic acid, and similar acids conventionally employed in the pharmaceutical industry. The salts are prepared by conventional neutralization or displacement methods routinely employed in polypeptide chemistry.

The tripeptide amides of this invention are analgesic agents capable of inducing analgesia in warm blooded animals in the same manner and by administration via the same routes including peripheral administration as the naturally occuring enkephalins and their tetra- and penta-peptide analogues.

The compounds of this invention are prepared by conventional solution or solid phase synthetic techniques well known to the polypeptide chemist. Following solid phase techniques, the tripeptide is constructed on a chloromethylated polystyrene resin beginning with protected glycine followed by coupling of the desired amino acid sequence. Following removal of the tripeptide from the resin support, it is coupled with the desired amine to afford its final product. By solution techniques, the tetrapeptide amide may be constructed by any desired combination of coupling to achieve the required amino acid sequence.

The optically active centers in the C-terminal amide moiety may be tailored to obtain predetermined absolute configuration by proper selection of reactants of known configuration. Thus, to obtain an S-α-(phenylmethyl)-1-peperazine-ethylamide of a tripeptide, the amine reactant is prepared by reaction of benzyloxycarbonyl (CBZ)protected L-phenylalanine with peperazine followed by removal of the protecting group and reduction of the amidic carbonyl with boron trihydride. The corresponding R configuration may be built into the C-terminal amide by employing D-Phe as the reactant. Similarly, where two chiral centers appear in the C-terminal amide moiety, proper selection of the initial reactants permits production of the tripeptide amides with known absolute configuration of the chiral centers in the amide.

The following examples illustrate the solution method for preparation of representative compounds of the invention.

EXAMPLE 1

$N^\alpha$-Benzyloxycarbonyl-D-alanyl-glycine ethyl ester

CBz-D-Ala-OH (67 g) was mixed with HCl . GlyOEt (45 g) N-hydroxybenzotriazole (50 g) and triethylamine (42 ml) and dissolved in a mixture of DMF-$CH_2Cl_2$ (600 ml, 1/1, v/v). The solution was cooled in an ice bath and then dicyclohexylcarbodiimide (66 g) was added and the mixture stirred overnight. The dicyclohexyl urea which separated was filtered off and the filtrate was evaporated to a small volume, excess water was added and the solid which precipitated was collected by filtration (70 g).

TLC silica gel precoated glass plates.
$R_f$(CHCl$_3$-MeOH, 25:1, v/v) 0.6.

EXAMPLE 2

$N^\alpha$-tert-Butyloxycarbonyl-O-benzyl-L-tyrosyl-D-alanyl-glycine ethyl ester The protected dipeptide CBz-D-Ala-Gly-OEt (70 g) was dissolved in EtOH (ca. 600 ml) mixed with 12N-aqueous HCl (25 ml) and 7 g of 10% Pd-C and the mixture was hydrogenated for 20 hours. The catalyst was filtered, the filtrate evaporated to dryness and the residue was dried by evaporation with abs. EtOH and benzene. The above product dissolved in 600 ml. DMF-$CH_3CN$ and mixed with Boc-Tyr(Bzl)OH (74 g), N-hydroxybenzotriazole (32 g) and neutralized with triethylamine to pH 7. The solution was cooled in an ice bath and treated with dicyclohexylcarbodiimide (DCC) (44 g.) for two hours in the cold then at room temperature overnight. The dicyclohexyl urea which separated was filtered off and the filtrate was evaporated to dryness. The residue was taken in a small volume of DMF and triturated with excess water to afford the title compound (52.7 g).

TLC silica gel precoated glass plates.
$R_f$(CHCl$_3$-MeOH, 4:1, v/v) 0.4.

EXAMPLE 3

$N^\alpha$-tert-Butyloxycarbonyl-O-benzyl-L-tyrosyl-D-alanyl-glycine

The protected tripeptide ester, Boc-Tyr(Bzl)-D-Ala-Gly-OEt (52.7 g) was dissolved in MeOH-dioxane, 1:1, v/v (200 ml) and then 100 ml. 1N NaOH was added. The mixture was stirred for 5 hours and then evaporated to a small volume. An excess of 10% citric acid solution was added and the gummy material which separated was taken in EtOAc. The organic layer was washed with water three times and dried over $Na_2SO_4$. The solvent was evaporated and the residue was triturated with diethyl ether to afford a solid which was recrystallized from MeOH-$H_2O$ (41 g), mp 95°–100° C.

TLC silica gel precoated glass plates (Merck).
$R_f$(MeOH) 0.66.
$R_f$(CHCL$_3$-MeOH, 4:1, v/v) 0.22.
$R_f$(CHCl$_3$-MeOH-AcOH, 85:10:5, v/v) 0.50.

EXAMPLE 4

1-(Benzyloxycarbonyl-L-phenylalanyl)-4-methyl piperazine

Benzyloxycarbonyl-L-phenylalanine (29.9 g., 0.1 mole) in 30 ml. $CH_2Cl_2$ was mixed with N-methylmorpholine (11.1 ml, 0.1 mole) and cooled at −15° C., then isobutyl chloroformate (10.3 ml, 0.08 moles) in 100 ml. $CH_2Cl_2$ was added and the mixture was stirred for 2 minutes after which time N-methylpiperazine (12.3 ml, 0.11 moles) was added. The mixture was stirred for 2 hours at −15° C. and then it was allowed to reach room temperature. The solution was washed with 5% $K_2CO_3$ solution three times, cold brine four times, dried over MgSO$_4$, and evaporated to dryness to afford an oil. This oil was taken in diethyl ether, some insoluble material was removed and then a solution of HCl in ethyl acetate was added to give a precipitate of the HCl salt, 30 g. The above salt was converted to the free base to afford 24 g. of oil (78% yield).

TLC silica gel precoated plates.
$R_f$(CHCl$_3$-MeOH-AcOH, 9:1:0.5, v/v) 0.41.

EXAMPLE 5

1-L-Phenylalanyl-4-methyl-piperazine

The material of the previous example was dissolved in 200 ml. and methanol mixed with 1 g of 10% Pd on charcoal catalyst and hydrogenated at 33 psi overnight. The catalyst was filtered off, the filtrate was evaporated to give an oil which was chromatographed through Alumina III and eluted with chloroform to afford the pure title compound, 14 g.

EXAMPLE 6

4-Methyl-S-α-(phenylmethyl)-1-piperazineethanamine

The compound of the previous example (11 g) was dissolved in 100 ml. of tetrahydrofuran and treated with 200 ml. of 1M-BH$_3$ in tetrahydrofuran. The solution was refluxed for 2 hours, quenched with 20 ml. of 2N-aqueous HCl, the excess tetrahydrofuran was distilled and the aqueous solution was refluxed for 20 hours and then left to stand at room temperature for 4 days. The H$_3$BO$_3$ was filtered off and the filtrate evaporated to dryness. The residue was flushed three times with some ethanol and then crystallized from ethanol-ether (1:3, v/v) to yield 9.89 g. solid.

TLC Avicel precoated glass plates.
$R_f$(n-butanol-water-AcOH, 4:1:1, v/v) 0.29.

Infrared spectrum does not show carbonyl absorption.

NMR (DMSO-d$_6$)δ7.83 (3H, s), 7.4 (5H, s).

Calc. for $C_{14}H_{26}N_3Cl_3.2H_2O$: C, 44.38%; H, 7.98%; N, 11.10%; Cl, 28%. Found: C, 44.95%; H, 7.20%; N, 11.23%; Cl, 29.17%.

EXAMPLE 7

N$^\alpha$-Butyloxycarbonyl-O-benzyl-L-tyrosyl-D-alanyl-N-[1-[(4-methyl-1-piperazinyl)methyl]-2-phenyl-ethyl]-glycinamide The protected tripeptide Boc-Tyr(Bzl)-D-Ala-Gly-OH (7.5 g) was dissolved in 200 ml. DMF and mixed with N-hydroxybenzotriazole (2.25 g), 4-methyl-S-$\alpha$-(phenylmethyl)-1-piperazine ethanamine hydrochloride (5.3 g), N-methylmorpholine (6.2 ml) and cooled in an ice-bath, then DCC (3.4 g) was added and the mixture was stirred at room temperature for 4 days. The DCCU which separated was removed by filtration. The filtrate was evaporated to dryness. The residue was taken in EtOAc and the organic solution was washed with 10% aqueous $K_2CO_3$ and water. The organic phase was dried over $K_2CO_3$ and evaporated to yield 10 g (yield 94%) of the title compound.

TLC, alumina No. 1 precoated glass plates.
R$_f$ 0.5 plus trace impurities.

The above material was chromatographed through 1 kg silica gel III, dry column, and eluted first with CHCl$_3$ then with CHCl$_3$—CH$_3$OH, 50:1, v/v. The top band was cut and extracted to yield 6.5 g (61%) of material.

TLC silica gel 60 precoated glass plates.
R$_f$(CHCl$_3$-MeOH, 4:1, v/v) 0.14.

EXAMPLE 8

0-Benzyl-L-tyrosyl-D-alanyl-N-[1-[(4-methyl-1-piperazinyl)methyl]-2-phenyl-ethyl]glycinamide The compound of the previous example (6.5 g) was treated with a mixture of trifluoroacetic acid-methylene chloride-anisole, 5:5:1, v/v, in an ice bath for 30 minutes. The solution was evaporated to dryness and the residue was triturated with diethyl ether. The solid was filtered, washed with diethyl ether and dried over $P_2O_5$ to yield 5 g. of the title compound.

TLC silica gel precoated glass plates.
R$_f$(n-Butanol-EtOAc-AcOH-H$_2$O, 1:1:1:1, v/v) 0:28.
NMR (DMSO-d$_6$) $\delta$1.05(3H, d), $\delta$2.65–3.1(overlapping m), 5.1 (2H, s), 6.9–7.3 (4H, m), 7.3 (5H, s), 7.44 (5H, s).

EXAMPLE 9

L-Tyrosyl-D-alanyl-N-[1-[(4-methyl-1-piperazinyl)methyl]-2-phenyl-ethyl]glycinamide The compound of the previous example (5 g) was dissolved in methanol and hydrogenated in a Parr shaker at 30 psi in the presence of 1 g of 10% Pd on charcoal, overnight. The catalyst was filtered and the filtrate was evaporated to dryness. The residue was triturated with diethyl ether to afford the title compound as di-trifluoroacetate salt. This material was passed through a column of Amberlite IR-45 (acetate form) and then lyophilized to afford the diacetate salt. This material was chromatographed through a column (2.5×200 cm) of Sephadex LH 20 and eluted with 5% acetic acid. Fractions 93–114 (5 ml each) were pooled and lyophilized to yield 2.8 g. of the title compound.

TLC silica gel precoated glass plates.
R$_f$(n-Butanol-EtOAc-AcOH-H$_2$O, 1:1:1:1, v/v) 0.21.
Amino acid analysis: Gly (1) 1, Ala (1) 0.91, Tyr (1) 1.02.

HPLC, K$^1$=5(4 mm×30 cm, $\mu$-Bondapak/C$_{18}$, 20% CH$_3$CN in water containing 4% glacial acetic acid and 0.4% NH$_4$OH).

EXAMPLE 10

N$^\alpha$-tert-Butyloxycarbonyl-N$^\alpha$-methyl-O-benzyl-L-tyrosyl-D-alanyl-glycine The tripeptide acid was prepared in a similar fashion as in examples 1–3 but in this case Boc-N-Methyl-Tyr(Bzl)OH was used instead of Boc-Tyr(Bzl)-OH. The product was recovered as an oily material.

TLC silica gel precoated glass plates (Merck).
R$_f$(CHCl$_3$-MeOH-AcOH, 9:1:0.5, v/v) 0.29. (CHCl$_3$-MeOH, 9:1, v/v) 0.63.
Amino acid analysis: Gly(1) 0.87, Ala(1) 1 [$\alpha$]$_D^{24.5}$-41.7 (C=0.975, CHCl$_3$).

EXAMPLE 11

1-(tert-Butyloxycarbonyl-N-methyl-L-phenylalanine)-4-methylpiperazine.

Tert-Butyloxycarbonyl-N-methyl-L-phenylalanine (14.1 g) was mixed with N-hydroxysuccinimide (6.4 g) and dicyclohexylcarbodiimide (11.5 g) in CH$_2$Cl$_2$ (ca. 500 ml) in an ice-bath and the mixture stirred for 15 minutes, after which time N-methylpiperazine (5.75 ml) was added dropwise and left to stand overnight at room temperature. The dicyclohexylurea which separated was filtered off and the filtrate was washed 3 times with 10% aq. K$_2$CO$_3$ and four times with water. The organic layer was dried over Mg$_2$SO$_4$ and evaporated to dryness to solid, yield 17.7 g. (98%), of the title compound. mp=91–3° C.

TLC silica gel precoated glass plates.
R$_f$(CHCl$_3$-MeOH, 4:1, v/v) 0.70.
R$_f$(n-Butanol-water-gl. AcOH, 4:1:1, v/v) 0.25.

EXAMPLE 12

1-(N-Methyl-L-phenylalanyl)-4-methyl piperazine trifluoroacetate salt

Material prepared as the previous example (21 g) was dissolved in 250 ml. CH$_2$Cl$_2$ and 50 ml. anisole, cooled at 5° C. and treated with 250 ml. trifluoroacetic acid for 30 minutes in the cold. The solution was evaporated to dryness. The residue was triturated with diethyl ether to afford the title compound (23 g. 79%) as solid. m.p. 150–3° C.

TLC Avicel precoated glass plates (Analtech).
R$_f$(n-Butanol-water-gl. AcOH, 4:1:1, v/v) 0.45.

EXAMPLE 13

N, 4-Dimethyl-S-$\alpha$-(phenylmethyl)-1-piperazine ethanamine hydrochloride salt Material of the previous example (11.5 g., 23.5 mmoles) was dissolved in 150 ml. dry tetrahydrofuran in the cold and mixed with 125 ml. of 1 M-BH$_3$ in tetrahydrofuran. The mixture was allowed to reach room temperature and then it was refluxed for two hours after which time it was chilled and quenched with 200 ml. of 2 N-HCl solution. The tetrahydrofuran was distilled off and the residue was refluxed for five hours then allowed to reach room temperature and evaporated to dryness in the rotary evaporator. The residue was flushed four times with 400 ml. ethanol and the insoluble material in hot ethanol (400 ml) was filtered to yield 3.9 g of the title compound. The filtrate was diluted with 600 ml. of diethyl ether to afford an additional 2.5 g. of the title compound as a trihydrochloride salt. Total yield 6.4 g. (76%) m.p. 240–2° C. (dec.).

TLC Avicel precoated glass plates.

$R_f$(n-BuOH-water-gl. acetic acid, 4:1:1, v/v) 0.31.

Elemental analysis: Calc. C, 50.63; H, 7.65; N, 11.81. Found: C, 49.80; H, 7.66; N, 11.56.

EXAMPLE 14

N$^\alpha$-Butyloxycarbonyl-N-methyl-O-benzyl-L-tyrosyl-D-alanyl-N,N-methyl[1-[(4-methyl-1-piperazinyl)methyl]-2-phenylethyl]-glycinamide $$\text{BOC}-\underset{\underset{CH_3}{|}}{N}-\underset{\underset{Bzl}{|}}{Tyr}-D-Ala-Gly-\underset{\underset{CH_3}{|}}{N}CH\underset{\underset{CH_2}{|}}{\underset{|}{\text{-}}}CH_2N\overset{\diagup\diagdown}{\underset{\diagdown\diagup}{\phantom{XX}}}NCH_3$$

The protected tripeptide Boc-N-Me-Tyr(Bzl)-D-Ala-Gly-OH (9.2 g., 18 mmoles) in 300 ml. CH$_2$Cl$_2$ was mixed with N-hydroxybenzotriazole (2.7 g., 20 mmoles) cooled in an ice-bath and then treated with dicyclohexylcarbodiimide (4.12 g., 20 mmoles). A solution of the piperazine compound of the previous example (6.4 g., 18 mmoles) in CH$_2$Cl$_2$ and N-methylmorpholine (5.9 ml, 54 mmoles) was added and the mixture was allowed to reach room temperature overnight. The dicyclohexylurea which separated was filtered and the filtrate was washed with 10% aq. K$_2$CO$_3$ 3 times water 3 times and dried over Na$_2$SO$_4$. The organic layer was evaporated to dryness to afford 12.2 g. of the crude title compound. This material was chromatographed through a dry column (2 liters silica gel II-III) and eluted with a mixture of CHCl$_3$-CH$_3$OH-AcOH, 9:1:0.5, v/v. The polar band was separated and extracted with elution solvent to give 4.2 g. of the title compound as white solid.

TLC silica gel precoated glass plates (Merck).

$R_f$(n-Butanol-water-gl. acetic acid, 4:1:1, v/v) 0.48.

EXAMPLE 15

N-methyl-L-tyrosyl-D-alanyl-N,N-methyl,[1-[(4-methyl-1-piperazinyl)methyl]-2-phenylethyl]glycinamide The material of the previous example (4.2 g) was slurried with 100 ml. 4.3 N-HCl in ethyl acetate containing 20 ml. of anisole and the mixture was stirred for one hour in an ice-bath. The mixture was evaporated to dryness and the residue was triturated with dry diethyl ether to afford 4 g. of the partially deprotected product.

TLC, silica gel precoated glass plates (Merck).

$R_f$(n-Butanol-water-gl. acetic acid, 4:1:1, v/v) 0.05.

Avicel precoated glass plates (Analtech).

$R_f$(n-Butanol-water-gl. acetic acid, 4:1:1, v/v) 0.80.

The above material was dissolved in 100 ml. methanol containing 5 ml. acetic acid and was hydrogenated overnight in the presence of 5% Pd on charcoal. The catalyst was filtered off and the filtrate was evaporated to a gummy material (3 g.). This material was purified first by partition chromatography through Sephadex G25 with the biphasic system n-Butanol-water-gl. acetic acid, 4:5:1, v/v, acid then by gel filtration through Sephadex LH 20 (elution with 10% aq. acetic acid) to give the title compound as a trihydrochloride salt (1.09 g)

Amino acid analysis: Ala (1) 1, Gly (1) 0.93.

The analgesic activity of the products of Examples 9 and 15 was demonstrated in the phenylbenzoquinone-induced writhing test according to the general procedure of Siegmund et al., Proc. Soc. Exp. Biol. Med., 95, 729–731 (1957), by establishing three groups of ten mice (Carworth farms) per group (18–27 g. body weight). The animals receive the compound being tested (Examples 9 and 15) subsubcutaneously. Five or 20 minutes later each animal received 0.25 milliliters of the writhing agonist (i.e. 0.02% solution of PBQ). The animals receiving the writhing agonist five minutes after the test compound are observed for a period of ten minutes beginning five minutes after the injection. The animals receiving the writhing agonist 20 minutes after the test compound are observed for ten minutes beginning five minutes after the injection. A compound is an analgesic if it inhibits writhing induced by phenyl benzoquinone.

The results obtained are as follows:

| Compound | ED$_{50}$ mg/kg. (confidence limits) | Time |
|---|---|---|
| L-tyrosyl-D-alanyl-N-[1-[(4-methyl-1-piperazinyl)methyl]-2-phenyl-ethyl]glycinamide | 1.05 (0.62–1.79) | 15 minutes |
|  | 4.60 (3.1–6.9) | 30 minutes |
|  | 6.20 (4.4–8.7) | 30 minutes |
| N-methyl-L-tyrosyl-D-alanyl-N,N-methyl, [1-[(4-methyl-1-piperazinyl)methyl]-2-phenyl-ethyl]glycinamide | 0.62 (0.37–1.03) | 30 minutes |

Following the procedure of Chang et al., Life Sciences, 18, 1473–82 (1976), the product of Example 9 exhibited a relative displacement potency of 1.3 with $^3$H-naloxone displacement of ED$_{50}$ of $1.36 \times 10^{-7}$ μM compared to morphine (RDP-1; ED$_{50}$ of $1.72 \times 10^{-7}$). The product of Example 15 demonstrated a relative displacement potency of 2.1 (morphine = 1).

Thus, the compounds of this invention are peripherally effective analgesic agents which may be administered to a warm-blooded animal orally or parenterally. The exact dose employed to achieve the desired level of analgesia will vary depending upon the particular compound employed and the route of administration. However, the determination of the precise dose needed to effect a desired degree of analgesia is readily determinable symptomatically by those skilled in the art.

What is claimed is:

1. A compound of the formula:

$$\underset{R^2}{\overset{R^1}{\diagdown}}N-Tyr-X^2-Gly-\underset{\underset{R^3}{|}}{N}-\underset{\underset{}{|}}{\overset{R^4}{|}}CH-\overset{R^5}{\underset{|}{C}}H-N\overset{\diagup\diagdown}{\underset{\diagdown\diagup}{\phantom{XX}}}N-R^6$$

in which

X$^2$ is D-Ala, D-Ser, D-Thr, D-Met, D-Cys, D-Trp, or D-Asn;

R$^1$ is hydrogen, alkyl of 1 to 6 carbon atoms, allyl, cyclopropylmethyl or cyclobutylmethyl;

R$^2$ is hydrogen or alkyl of 1 to 6 carbon atoms;

R$^3$ is hydrogen or alkyl of 1 to 6 carbon atoms;

R$^4$ is isobutyl, cyclohexyl, benzyl, p-halobenzyl or p-nitrobenzyl;

R$^5$ is hydrogen or alkyl of 1 to 6 carbon atoms; and

R[6] is hydrogen, alkyl of 1 to 6 carbon atoms, 2-hydroxyethyl, benzyl, diphenylmethyl, phenyl, p-halophenyl, p-nitrophenyl,

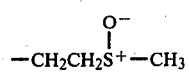

or -CH₂CH₂SCH₃;

or a pharmaceutically acceptable salt thereof.

2. A compound of claim 1 which is L-tyrosyl-D-alanyl-N-[1-[(4-methyl-1-peperazinyl)methyl]-2-phenylethyl]glycinamide or a pharmaceutically acceptable salt thereof.

3. A compound of claim 1 which is N-methyl-L-tyrosyl-D-alanyl-N,N-methyl,[1-[(4-methyl-1-piperazinyl)methyl]-2-phenylethyl]glycinamide or a pharmaceutically acceptable salt thereof.

* * * * *